(12) United States Patent
Kamen et al.

(10) Patent No.: US 11,154,698 B2
(45) Date of Patent: Oct. 26, 2021

(54) MICRONEEDLE SYSTEMS AND APPARATUS

(75) Inventors: Dean Kamen, Bedford, NH (US); Larry B. Gray, Merrimack, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 12/197,583

(22) Filed: Aug. 25, 2008

(65) Prior Publication Data
US 2009/0099522 A1   Apr. 16, 2009

Related U.S. Application Data (60) Provisional application No. 60/966,174, filed on Aug. 24, 2007.

(51) Int. Cl.
*A61M 37/00* (2006.01)

(52) U.S. Cl.
CPC . *A61M 37/0015* (2013.01); *A61M 2037/0061* (2013.01)

(58) Field of Classification Search
CPC .. A61M 2037/0053; A61M 2037/0023; A61M 2037/0061; A61M 37/0015; A61M 2037/003; A61K 9/0021
USPC ........ 604/892.1, 173, 890.1, 43, 191, 46, 47
See application file for complete search history.

(56) References Cited

U.S. PATENT DOCUMENTS

| | | | |
|---|---|---|---|
| 4,741,736 A | 5/1988 | Brown | |
| 5,855,801 A | 1/1999 | Lin et al. | |
| 6,334,856 B1 | 1/2002 | Allen et al. | |
| 6,485,461 B1 * | 11/2002 | Mason ................. | A61M 5/141 604/132 |
| 6,503,231 B1 | 1/2003 | Prausnitz et al. | |
| 6,582,393 B2 | 6/2003 | Sage | |
| 6,589,229 B1 * | 7/2003 | Connelly et al. .......... | 604/890.1 |
| 7,027,478 B2 | 4/2006 | Ackley | |
| 7,226,439 B2 | 6/2007 | Prausnitz et al. | |
| 7,344,499 B1 | 3/2008 | Prausnitz et al. | |
| 7,416,541 B2 | 8/2008 | Yuzhakov et al. | |
| 7,429,258 B2 * | 9/2008 | Angel et al. ................. | 604/173 |
| 7,429,333 B2 | 9/2008 | Chiou et al. | |
| 2002/0169416 A1 * | 11/2002 | Gonnelli ........... | A61M 5/14248 604/142 |
| 2003/0153900 A1 * | 8/2003 | Aceti et al. ................ | 604/890.1 |
| 2004/0186419 A1 | 9/2004 | Cho | |
| 2005/0065463 A1 | 3/2005 | Tobinaga et al. | |

(Continued)

OTHER PUBLICATIONS

International Search Report with Written Opinion, dated Nov. 19, 2008, received in international patent application No. PCT/US08/74189, 8 pages.

*Primary Examiner* — Bhisma Mehta
*Assistant Examiner* — Weng Lee
(74) *Attorney, Agent, or Firm* — Reid Knott Cunningham (57) ABSTRACT

A medical system. The medical system includes at least one compartment for a fluid, a fluid path and at least one microneedle fluidly connected to the at least one compartment by the fluid path. A medical infusion system is also disclosed. The system includes a wearable housing, at least one non-pressurized compartment for a fluid contained within the housing, at least one fluid path fluidly connected to the at least one compartment and at least one microneedle fluidly connected to the at least one compartment by the fluid path wherein the fluid path extends through the microneedle.

14 Claims, 10 Drawing Sheets

(56) References Cited

U.S. PATENT DOCUMENTS

| | | | |
|---|---|---|---|
| 2005/0100937 A1* | 5/2005 | Holmes | A61B 5/0024 |
| | | | 435/6.12 |
| 2005/0118388 A1* | 6/2005 | Kingsford | A61B 17/205 |
| | | | 428/99 |
| 2005/0137531 A1 | 6/2005 | Prausnitz | |
| 2005/0273059 A1* | 12/2005 | Mernoe | A61M 5/14248 |
| | | | 604/180 |
| 2006/0015144 A1* | 1/2006 | Burbank | A61B 17/064 |
| | | | 606/219 |
| 2006/0219576 A1* | 10/2006 | Jina | 205/792 |
| 2007/0021717 A1* | 1/2007 | Gabel et al. | 604/93.01 |
| 2008/0119707 A1* | 5/2008 | Stafford | A61B 5/14503 |
| | | | 600/365 |
| 2008/0221408 A1 | 9/2008 | Hoarau et al. | |
| 2008/0269584 A1 | 10/2008 | Shekalim | |
| 2008/0269666 A1* | 10/2008 | Wang et al. | 604/21 |
| 2008/0275468 A1 | 11/2008 | Chuang et al. | |
| 2008/0281273 A1 | 11/2008 | Angel et al. | |
| 2008/0287858 A1 | 11/2008 | Duan | |
| 2009/0131860 A1* | 5/2009 | Nielsen | 604/66 |
| 2010/0100005 A1* | 4/2010 | Mir et al. | 600/556 |

\* cited by examiner

MICRONEEDLE SYSTEMS AND APPARATUS

CROSS REFERENCE TO RELATED APPLICATIONS

The present application is a Non-provisional Applications which claims priority from U.S. Provisional Patent Application 60/966,174, filed Aug. 24, 2007.

TECHNICAL FIELD

The present invention relates to microneedles and more particularly, to microneedle systems and apparatus.

BACKGROUND INFORMATION

Microneedles may be formed as arrays of varying densities. One such microneedle and production technique thereof is described in U.S. Pat. Nos. 6,558,361 and 6,533,949, which are both herein incorporated by reference in their entireties.

Microneedles may be used, for example, to transport fluids through a biological barrier, and are desirable for example because of the reduction in the amount of pain experienced by a human or other mammal receiving the fluids through a needle. Accordingly, there is a need for microneedles and system for use in transporting fluids, including insulin, through a biological barrier. There is also a need for a less painful analyte sensing device.

SUMMARY

In accordance with one aspect of the present invention, a medical system is disclosed. The medical system includes at least one compartment for a fluid, a fluid path and at least one microneedle fluidly connected to the at least one compartment by the fluid path.

Some embodiments of this aspect of the present invention may include one or more of the following: wherein the compartment is a non-pressurized compartment; wherein the fluid path extends through the microneedle; where the at least one microneedle is an analyte sensor; wherein the at least one microneedle having at least two appendages whereby the appendages provide for microneedle retention in a patient; wherein the at least one compartment for a fluid is contained within a housing; wherein the housing is a wearable housing; and/or wherein the housing is an infusion pump.

In accordance with another aspect of the present invention, a medical infusion system is disclosed. The system includes a wearable housing, at least one non-pressurized compartment for a fluid contained within the housing, at least one fluid path fluidly connected to the at least one compartment and at least one microneedle fluidly connected to the at least one compartment by the fluid path wherein the fluid path extends through the microneedle.

Some embodiments of this aspect of the present invention may include one or more of the following: wherein the at least one microneedle including a body portion and at least two appendages whereby said appendages provide for microneedle retention in a patient; wherein the body portion of the microneedle is made from a first material and the appendages are made from a second material wherein the second material is different from the first material and wherein the second material is dissolvable in a patient; and/or wherein the system further includes at least one microneedle analyte sensor connected to a path, wherein the path is connected to the wearable device.

In accordance with one aspect of the present invention, a medical infusion and sensing system is disclosed. The system includes a wearable housing, at least one non-pressurized compartment for a fluid contained within the housing, at least one fluid path fluidly connected to the at least one compartment, at least one microneedle fluidly connected to the at least one compartment by the fluid path wherein the fluid path extends through the microneedle; and at least one microneedle analyte sensor attached to a path, the path attached to the housing.

Some embodiments of this aspect of the present invention may include one or more of the following: wherein the wearable housing includes a reusable portion and a disposable portion; wherein the at least one microneedle comprising a body portion and at least two appendages whereby the appendages provide for microneedle retention in a patient; wherein the body portion of the microneedle is made from a first material and the appendages are made from a second material wherein the second material is different from the first material and wherein the second material is dissolvable in a patient; wherein the at least one compartment comprising at least one flexible portion; wherein the at least one compartment comprising a septum; wherein the system further includes a pumping mechanism for pumping fluid from the at least one compartment through the fluid path; and/or wherein the pumping mechanism is actuated using at least one shape memory actuator.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

"Fluid" shall mean a substance, a liquid for example, that is capable of flowing through a flow line.

A "patient" includes a person or animal who receives fluid from a fluid delivery device, whether as part of a medical treatment or otherwise.

"Analyte sensor" shall mean any sensor capable of determining the presence of an analyte in a patient. The embodiments of analyte sensors include, but are not limited to, sensors capable of determining the presence of any viral, parasitic, bacterial or chemical analyte. The term analyte includes glucose. An analyte sensor may communicate with other components within the fluid delivery device (e.g., a controller in a non-disposable portion) and/or with a remote controller.

An exemplary use of embodiments of the device is for the delivery of insulin to diabetic patients, but other uses include delivery of any fluid, as described above. Fluids include analgesics to those in pain, chemotherapy to cancer patients and enzymes to patients with metabolic disorders. Various therapeutic fluids may include small molecules, natural products, peptide, proteins, nucleic acids, carbohydrates, nanoparticulate suspensions, and associated pharmaceutically acceptable carrier molecules. Therapeutically active molecules may be modified to improve stability in the delivery device (e.g., by pegylation of peptides or proteins). Although illustrative embodiments herein describe drug-delivery applications, embodiments may be used for other applications including liquid dispensing of reagents for high throughput analytical measurements such as lab-on-chip applications and capillary chromatography. For purposes of description below, terms "therapeutic" or "fluid" are used interchangeably, however, in other embodiments, any fluid, as described above, can be used. Thus, the device and description included herein are not limited to use with therapeutics. In addition, the microneedles and devices and systems described herein may be used as an analyte sensor, either together with a fluid delivery device or separate.

Figure 1:
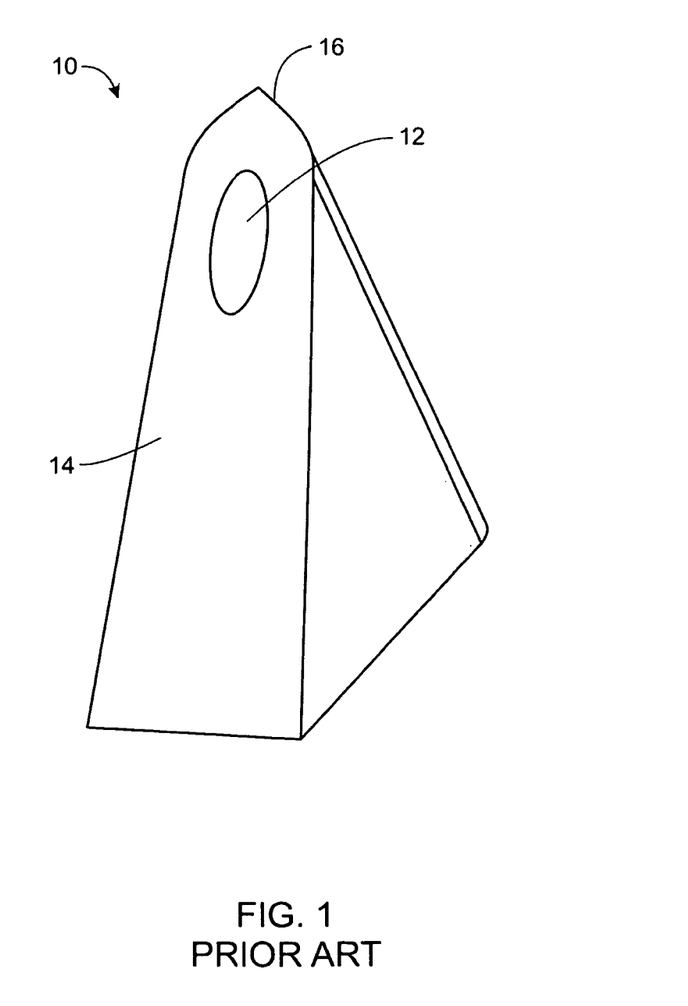
FIG. 1 is a front view of a prior art microneedle.
Figure 3A:
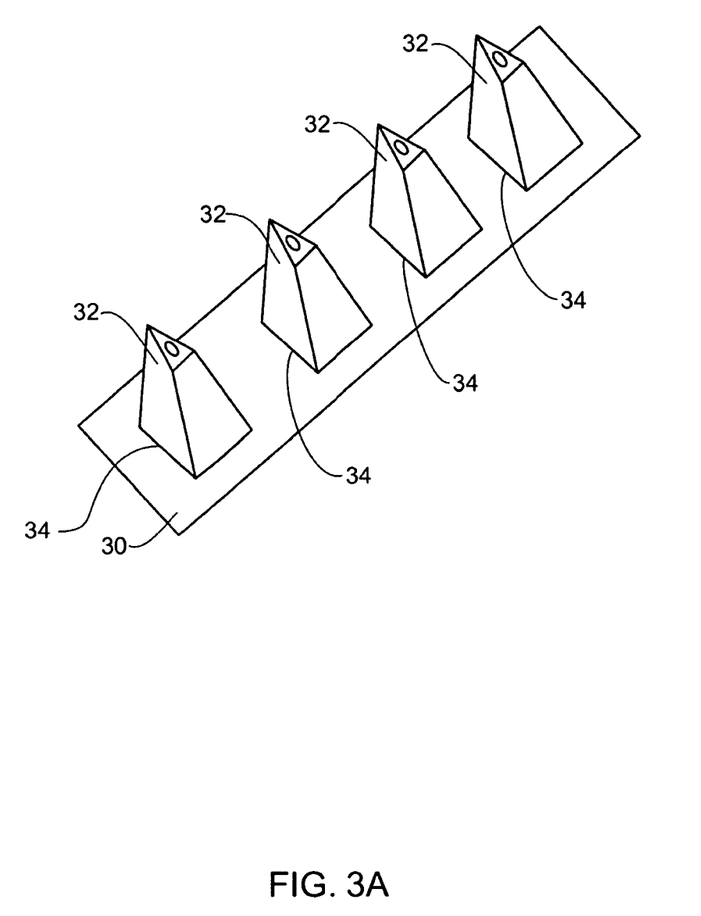
FIG. 3A is a is a front view of an array of microneedles.

Referring first to FIG. 1, a microneedle 10 as one known in the art is shown. Although shown alone, the microneedle 10, in practice, may be attached to a substrate. The microneedle 10 includes a body 14 and in some embodiments, at least one slot 12 leading to an open shape having an included area. The slot 12 serves as a fluid transfer aperture. In many instances, the microneedle 10 is grown as part of an array (see FIG. 3). In some embodiments, at least one microneedle is connected to a substrate (not shown).

In some embodiments, the tip 16 of the microneedle apparatus 10 may be asymmetrical with a non-hollow penetrating portion which extends beyond the slot 12. The shape of the top 16 helps prevent plugging of the microneedle during insertion into the patient. The shape of the tip 16 also facilitates withdrawal of the microneedle apparatus 10 from the patient as well as facilitates and delivery of the fluids. The microneedle apparatus 10 structure, in various embodiments, is analogous to the beveled ends of conventional syringe needles which are known to be effective penetrating tissue without becoming blocked.

Figure 2:
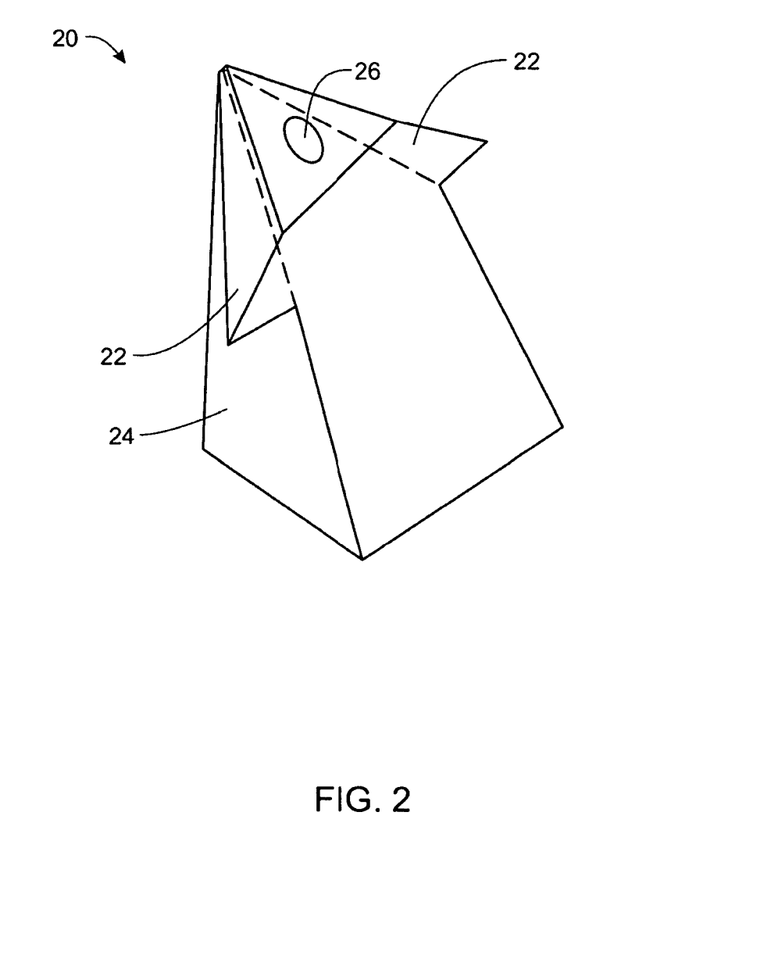
FIG. 2 is a front view of a microneedle with appendages/fixtures.

Referring now to FIG. 2, one exemplary embodiment of the microneedle apparatus 20 is shown. In this embodiment, the microneedle apparatus 20 includes appendages/fixtures 22 and a body 24. Although the appendages 22 are shown in FIG. 2 as having one shape, in other embodiments, the appendages 22 may be any shape desired including having greater or reduced angles with respect to the body 24 of the microneedle 20 or including a more hook-like shape. In some embodiments of this embodiment of the microneedle apparatus 20, the microneedle apparatus 20 also includes a slot 26, however, in some embodiments, the microneedle apparatus does not include a slot 26.

In one exemplary embodiment, the appendages 22 are made from a different material than the body 24 of the microneedle. In some embodiments, the appendages 22 are made from a biologically compatible dissolvable material. Thus, in these embodiments, the appendages 22 may be made from any material that is biologically compatible and that will dissolve once inside the body of a patient. Thus, in these embodiments, the appendages 22 will dissolve or disintegrate over a particular time while the remainder of the microneedle will not.

Biologically compatible materials include but are not limited to compositions made with salt, glucose and starch. In these embodiments, the material composition is capable of being formed into an appendage shape and presented into the derma of a patient. The appendage then prevents the microneedle from unwontedly being pulled from the patient and after the passage of a predetermined period of time, the appendages dissolve or disintegrate facilitating the removal of the microneedles from the patient.

The appendages 22 may be bonded to a microneedle using any method. In some embodiments, the appendages 22 additionally are coated or include in their composition an antimicrobial or antibiotic composition. However, in other embodiments, the microneedle and appendage are formed together. In some embodiments, the microneedle is also made from a biologically dissolvable material and thus, the microneedle may disintegrate while in the patient's skin, over a time period.

The microneedles may be made from any material desired, including one or more materials, including but not limited to, stainless steel, any metallic material, polymers, biological materials that dissolve within the patient, and materials may include one or more layers.

In some embodiments, for example, those described below where the microneedle apparatus is used as an analyte sensor, the microneedle may be formed with additional components on the outside and or inside. Those components would be any of those used in analyte sensors.

Referring now to FIG. 3A, a substrate 30 defines a substantially planar front face 34 of the microneedle devices 32. A plurality of microneedles 32 project from the front face 34. Each microneedle has, for example, a maximum width dimension w measured parallel to the front face of no more than 400 micrometers and a maximum height dimension h, measured perpendicular to the front face 34, of no more than about 2 mm.

In some embodiments, the substrate includes more than one layer. A first layer may include the front face of the microneedles and a second layer including a layer of adhesive for adherence to a patient's skin. In some embodiments, the first layer includes one part of a fluid pathway on its underside (or fluid path) and the second layer includes a mating part of the fluid path on its inner side. In some embodiments, the second layer includes an adhesive layer or a layer of material used for adhesion or attachment, on the outer side.

Figure 3B:
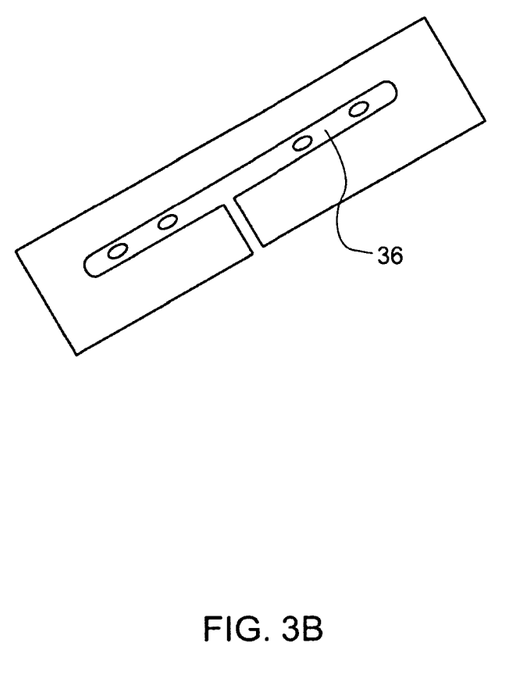
FIG. 3B is a cross sectional view of a substrate fluid path.

Referring now to FIG. 3B, in some embodiments, a fluid path 36, associated with each of the microneedles 32, extends through at least part of the substrate 30. The fluid path is configured to provide a fluid flow path for transport of fluid from a source to the microneedle (not shown) and through a hole in the biological barrier formed by the corresponding microneedle 32. The fluid path shown represents some embodiments, however, in other embodiments, more than one fluid source may be used, and/or in some embodiments, the fluid path may vary. For example, if more than one fluid source is used, the fluid path may be configured such that one or more microneedles are fluidly connected to one or more fluid sources.

The microneedles apparatus shown in FIG. 2, in practice, may be incorporated alone or as an array of two or more. In one embodiment, the microneedle apparatus is used on the infusion end of an infusion set or cannula, where the reservoir end is connected to a reservoir or compartment that holds a fluid. One embodiment of this embodiment of the apparatus is where one or more microneedles apparatus are in fluid connection with the reservoir or compartment.

The height of the microneedles, in some embodiments, is chosen to allow penetration to only the stratum corneum (SC) and epidermis derma layers, avoiding contact with nerves. For example, in some embodiments, the maximum height h is preferably chosen to be no more than about 200 micrometers. However, for some applications, deeper penetration may be desired, and longer microneedles may be used.

Figure 3C:
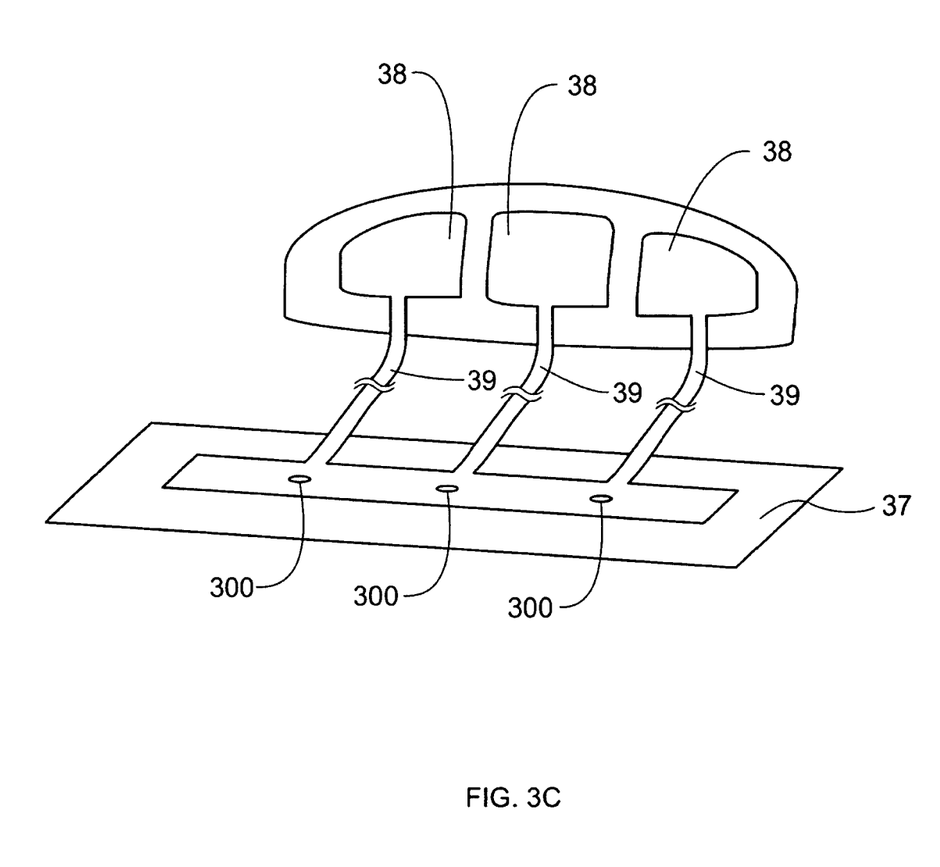
FIG. 3C is a cross sectional view of a multi-reservoir device fluidly connected to a microneedle substrate fluid path.

Referring now to FIG. 3C, one embodiment includes a multi-fluid delivery system. The system includes a manifold having multiple separate compartments 38, each capable of receiving a fluid and containing the fluid so as to not be contaminated by any adjacent compartment fluid. Although shown in this figures with three compartments 38, the number of compartments may vary in the various embodiments, for example, the system may include one, two, three, four or more compartments 38. Each compartment 38 is fluidly connected to at least one microneedle (not shown). The microneedles are connected to a substrate 37. The fluid is transferred from the compartment 38 to the microneedles by way of a fluid line 39 and an opening 300 in the fluid line to the microneedle. The fluid line 39 may be any length desired, for example, from as short as a couple mm to a meter or more. In some embodiments, greater than one microneedle is fluidly connected to each of the compartments 38 so as to transfer larger volumes of fluid either quicker or over a greater surface area to a patient. The fluid contained in the compartments 38 may be any of the fluids described above. The compartments may be any compartment known in the art to hold a fluid or to hold the particular fluid. In some embodiments, the compartments are reservoirs such as those described in U.S. Patent Application 2007/0219480 published Sep. 20, 2007 which is herein/hereby incorporated by reference in its entirety.

In some embodiments, the compartments are housed in a patch-pump such as the various ones described in U.S. Patent Application 2007/0219480. The various reservoirs (also called compartments) may each contain a different fluid, or two or more may contain redundant fluids. In some embodiments, one compartment contains insulin while the others contain glucagon and, in some embodiments, another compartment may contain glycogen.

Figure 6:
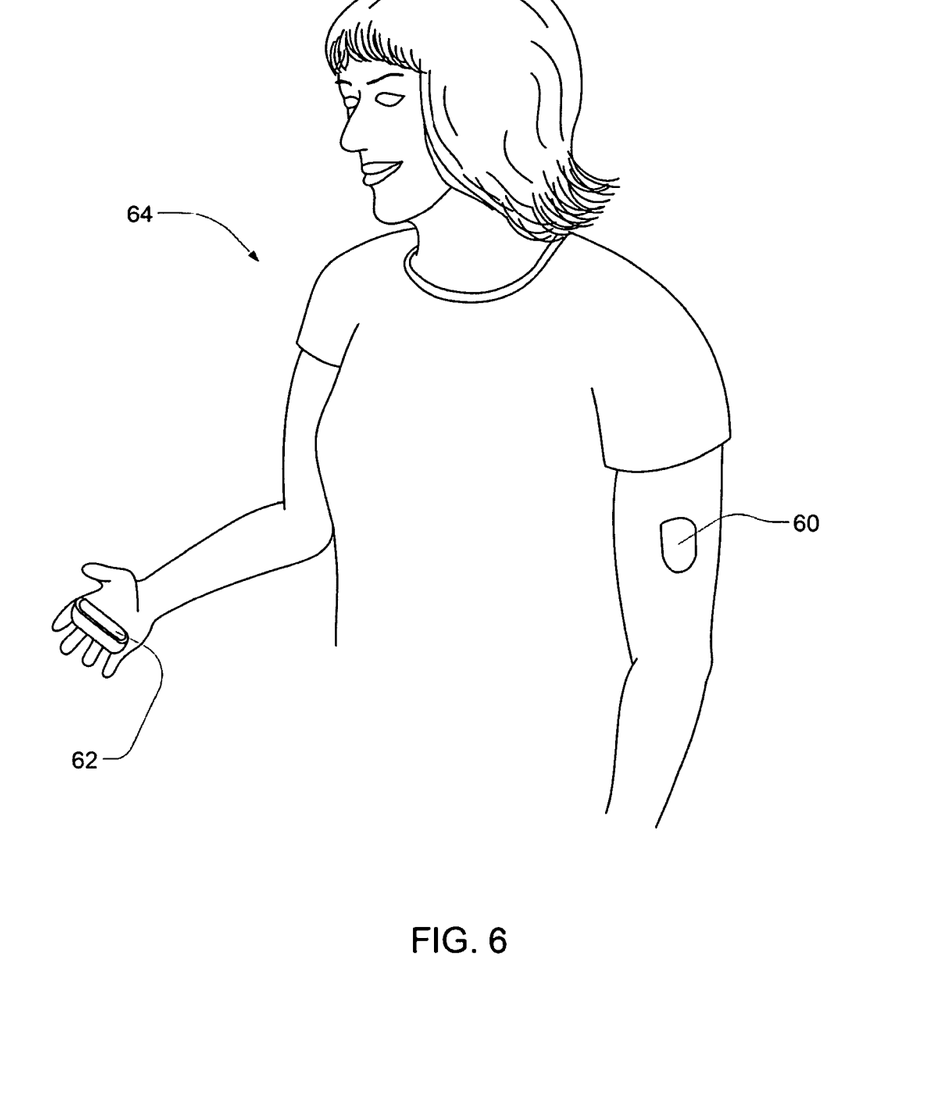
FIG. 6 depicts a patient with a device and hand-held user interface assembly.

Referring now to FIG. 6, in some embodiments, the compartments or reservoirs are contained within a housing 60, which may be a wearable patch pump or wearable housing, i.e., the housing attaches directly to a patient or the housing may be worn by a patient, i.e., in a pocket or clipped to a patient's clothing. In some embodiments, the delivery of the fluids from the compartments is controlled by a remote hand-held controller 62. The patient 64 may therefore control the delivery of the fluids by a remote hand-held controller 62. In some embodiments, the remote hand-held controller may be controlled by a person other than the patient. However, in some embodiments, the housing may be a bedside housing or other housing that may/may not be wearable. The user interface with the patient may be included on the housing itself and/or on a remote hand-held device.

Figure 7A:
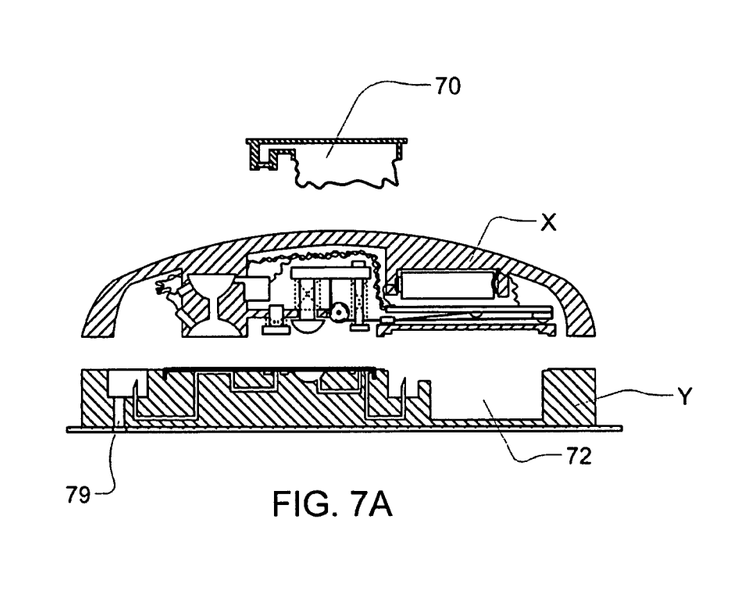
FIGS. 7A-7D show cross section schematics of a device with a compartment.
Figure 7B:
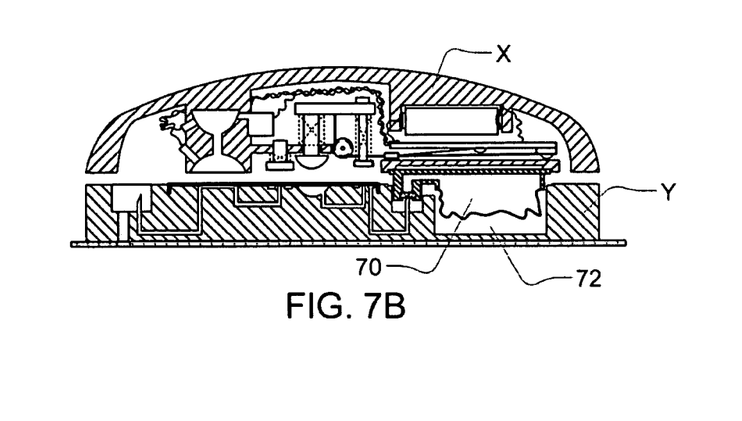
Figure 7C:
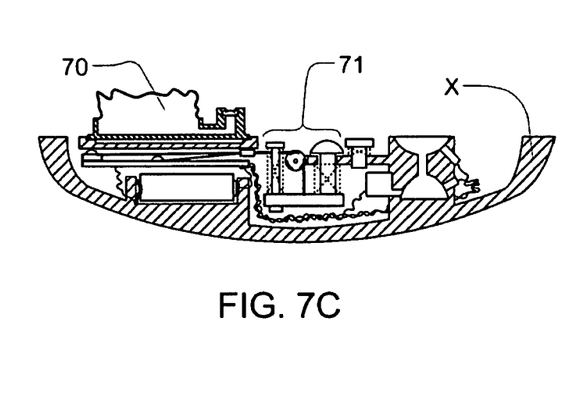
Figure 7D:
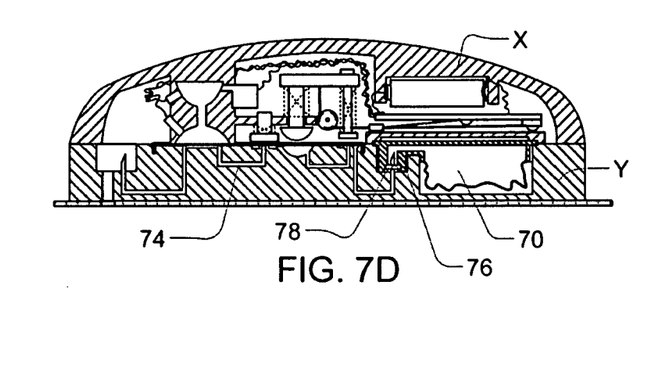

Referring now to FIGS. 7A-7D, in some embodiments, the housing includes two portions, an X and a Y portion. In some embodiments, the X portion is reusable while the Y portion is disposable. The X and Y portion mate to form a pumping apparatus. The compartments, or reservoir, 70, may be flexible, as shown. The compartment 70 fits into a space 72 of the Y portion. However, in some embodiments, as shown in FIG. 7C, the compartment 70 attaches first to the X portion and then fits into a space in the Y portion, as shown in FIG. 7D.

As shown in FIG. 7D, in some embodiments, the compartment 70 is fluidly connected to a fluid path 74 by a needle 76 or object penetrating a septum 78 on the compartment.

Although as shown in FIG. 7A-7D, the housing contains one compartment, in various other embodiments, the housing includes multiple compartments, each including a fluid path, and a means of fluidly connecting the compartment to the fluid path.

As shown in FIG. 7A, the fluid path includes an exit 79. In various embodiments, the fluid path would extend past the exit 79 and eventually connect to a microneedle.

The fluid in the compartment may be pumped through the fluid line through different means. One pumping mechanism 71 is shown in FIGS. 7A-7D, although other mechanisms may be used.

Figure 8:
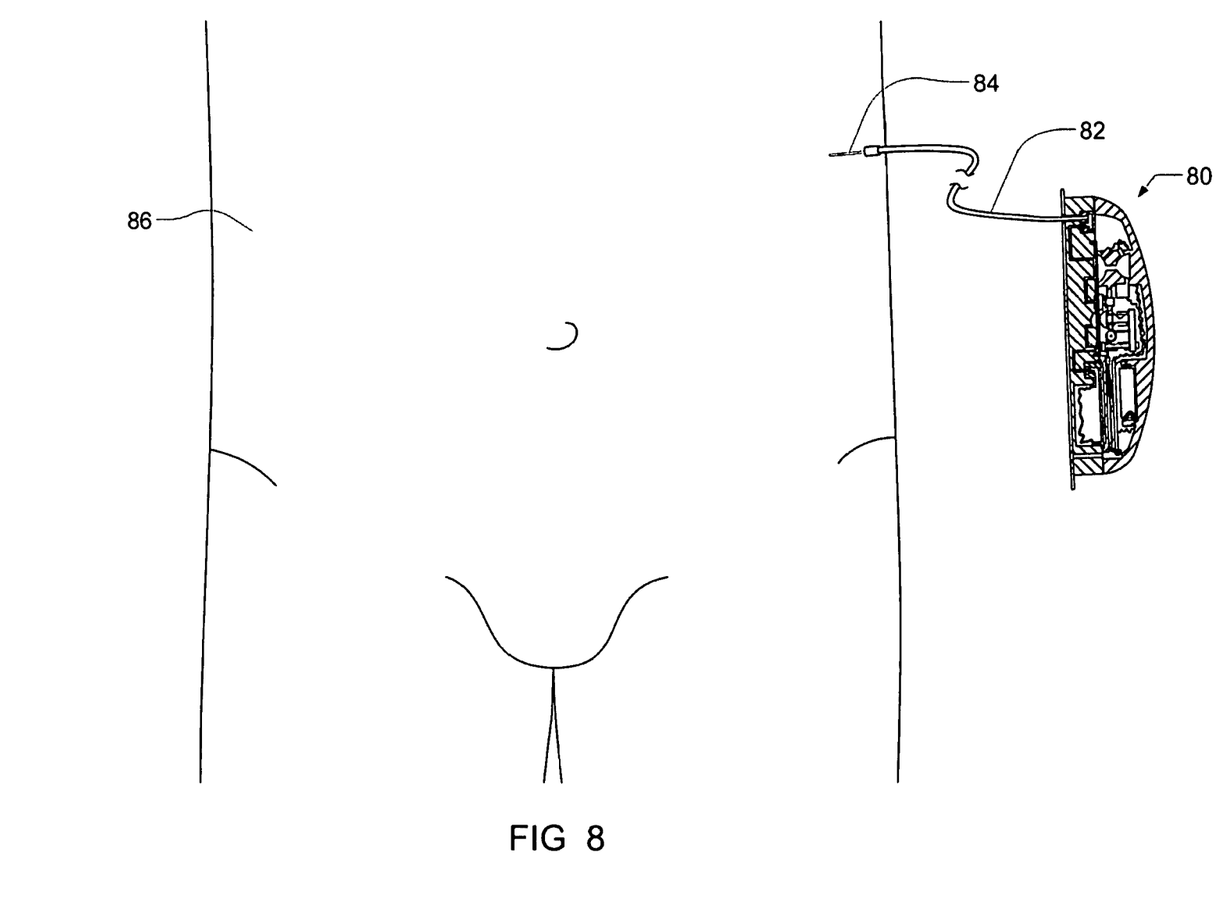
FIG. 8 is a schematic of one embodiment of the device connected to a patient.

Referring now to FIG. 8, a device 80 including a fluid compartment is shown. A fluid path 82 extends from the exit of the device 80 and through a microneedle 84 which has been inserted into a patient 86. In various embodiments, the device may include more than one compartment including more than one exit, and/or more than one fluid line extending from the device, ending in a microneedle which may be inserted into a patient.

Typical embodiments include a reservoir or compartment for holding a supply of fluid. In the case of insulin, the reservoir may be conveniently sized to hold an insulin supply sufficient for delivery over one or more days. For example, a reservoir may hold about 1 to 2 ml of insulin. A 2 ml insulin reservoir may correspond to about 3 days supply for about 90% of potential users. In other embodiments, the reservoir can be any size or shape and can be adapted to hold any amount of insulin or other fluid. In some embodiments, the size and shape of the reservoir is related to the type of fluid the reservoir is adapted to hold. The fluid reservoir may be eccentrically or irregularly shaped and/or may be keyed in order to deter incorrect installation or usage.

In some embodiments, the reservoir or compartment may be a partially collapsible non pressurized reservoir. This may advantageously prevent the buildup of air in the reservoir as the fluid in the reservoir is depleted. The reservoir may be connected to the fluid path through a septum (not shown). Air buildup in a vented reservoir could prevent fluid egress from the reservoir, especially if the system is tilted so that an air pocket intervenes between the fluid contained in the reservoir and the septum of the reservoir. Tilting of the system may be expected during normal operation when used in a wearable device.

The flow of fluid from the various compartments through the fluid lines 39 may be controlled by active valves or passive valves. In some embodiments a pumping mechanism may be located downstream from the compartment to actuate the valves. The configuration may be similar to the pumping mechanisms described in U.S. Patent Application 2007/0219480. In some embodiments, the pumping mechanism is actuated using at least one shape memory actuator (e.g., a conductive shape-memory alloy wire) that changes shape with temperature. The temperature of the shape-memory actuator(s) may be changed with a heater, or more conveniently, by application of an electric current. In one embodiment, the shape memory actuator is a shape memory wire constructed of nickel/titanium alloy, such as NITINOL™ or FLEXINOL®.

The substrate 37 together with the plurality of microneedles may be akin to a cannula such as those used with insulin pumps and other infusion delivery devices. The substrate may include a second layer over the fluid pathways. In these embodiments, the fluid paths are sandwiched within the substrate. The substrate may also include an adhesive layer on the patient side of the substrate. In some embodiments, the cannula may also be incorporated into a spring-based auto-inerter system similar to those found in the art.

Figure 4:
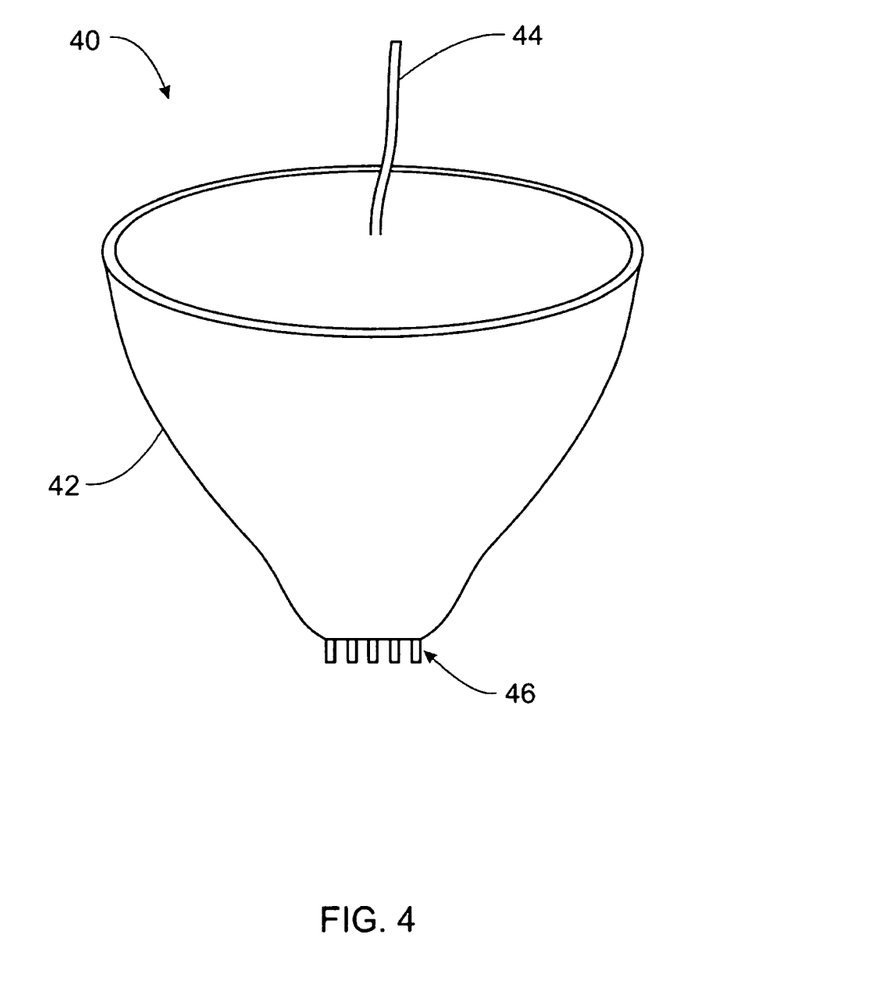
FIG. 4 is a front view of a microneedle array on a pen needle.

Referring now to FIG. 4, an insulin pen apparatus 40 is shown. This embodiment includes at least one microneedle 46 on the end of a pen housing 42. Thus, in some embodiments, the substrate is attached to the end of the pen housing. In other embodiments, the microneedles may be manufactured on a substrate that is a pen housing. The microneedle(s) 46 are fluidly connected to a needle 44. The pen apparatus 40 may be attached to the end of an insulin pen, for example, one known in the art, and in this attachment process, the needle 44 penetrates the septum of the insulin pen. Insulin is able to flow from the insulin pen, through the needle and through the microneedles 46 into the patient. Greater numbers of microneedles 46 enable quicker delivery of a volume of insulin and will allow delivery over a greater patient surface area. The microneedles 46 used in these embodiments may be any microneedles including those described and shown above with respect to FIGS. 1-2.

In another embodiment, at least one microneedle, for example, in some embodiments, the embodiments shown in either FIG. 1 or FIG. 2, is incorporated as part of an analyte sensor. The at least one microneedle may be used as an introduction needle for the analyte sensor or in conjunction with the analyte sensor. In some embodiments, the microneedles may be incorporated as a fluid delivery device to fluids to provide for example, insulin therapy, chemotherapies, vitamins, painkillers, antibacterials, antimicrobials or any other therapeutic or nutritive fluid or compound therapy. The microneedles as shown in FIG. 1 or FIG. 2, and other known in the art, may be used in conjunction with an insulin pump, whether a syringe pump or a patch pump. The microneedles may be used in conjunction with any device that delivers a therapeutic or nutritive fluid and may be used to deliver more than one type of fluid as part of the same device, delivering the fluid(s) when requested and of the volume requested, either by a patient, microprocessor or device. In some embodiments, the microneedles are used to deliver a given volume of fluid quicker or over a larger surface area.

Figure 5:
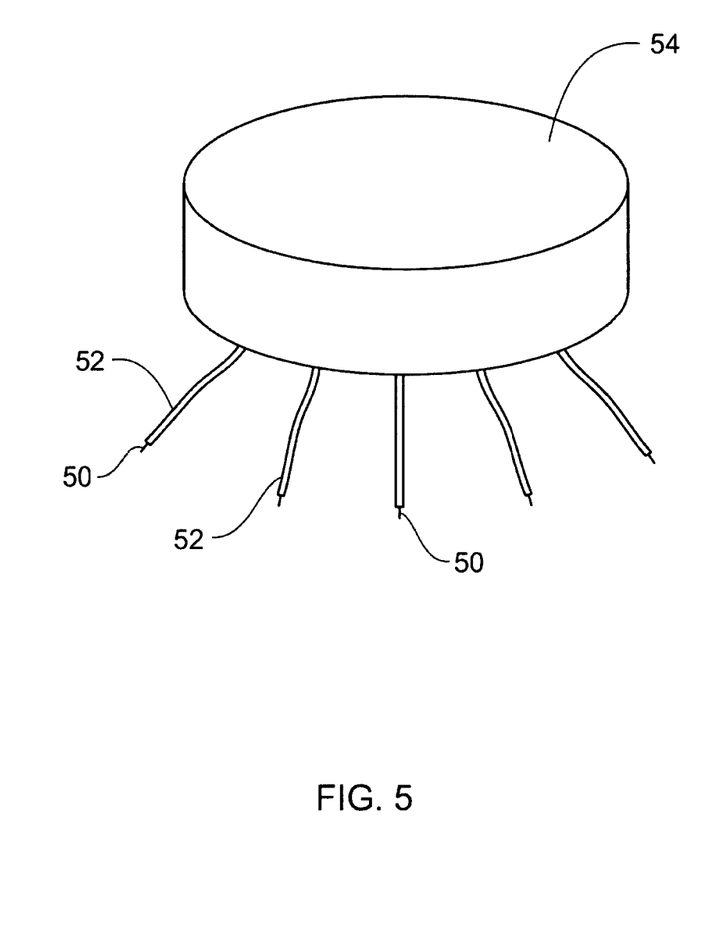
FIG. 5 is an apparatus with a manifold and multiple microneedles.

Referring now to FIG. 5, in one embodiment, at least one microneedle 50 is located on the end of at least one fluid path 52 or sensor paths. In embodiments including multiple fluid paths 52, the fluid paths 52 and paths 52 are spaced appropriate for delivery, i.e. depending on the fluid(s) being delivered and/or the sensor; it may be desired for the various fluid paths and paths to be a given/specific distance from one another. In some embodiments, paths are used to hold a microneedle apparatus 50 which may be an analyte sensor. Thus, in some other embodiments, one or more fluid paths 52 contain at least one microneedle 50 for fluid delivery of either the same or different fluid, and at least one arm contains at least one microneedle for analyte sensing. The manifold or housing 54 contains one or more fluids to be delivered and can additionally include valves in the fluid lines for pulsed or controlled delivery. Additionally, the manifold may be connected to a pumping mechanism that may control the pulses and provide for controlled volumetric delivery of fluids. In various embodiments, the length of the fluid paths or path and the spacing between them may be any length desired for the particular purpose.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

The invention claimed is:

1. A medical system comprising:
    at least one at least partially collapsible reservoir for an infusible fluid comprising an integral septum;
    a fluid path fluidly connected to the at least one partially collapsible reservoir; and
    at least one microneedle fluidly connected to the at least one partially collapsible reservoir by the fluid path,
    wherein the at least one partially collapsible reservoir is fluidly connected to the fluid path by at least one needle penetrating the septum on the at least one partially collapsible reservoir,
    wherein the at least one microneedle having a body portion and at least two appendages,
    wherein the body portion is made from a first material and the at least two appendages are made from a second material, wherein the second material is different from the first material,
    wherein the second material is dissolvable, and
    wherein the at least two appendages provide for microneedle retention.

2. The medical system of claim 1 wherein the at least one partially collapsible reservoir is a non-pressurized at least partially collapsible reservoir.

3. The medical system of claim 1 wherein the fluid path extends through the microneedle.

4. The medical system of claim 1 wherein the at least one microneedle is an analyte sensor.

5. The medical system of claim 1 wherein the at least one at least partially collapsible reservoir for a fluid is contained within a housing.

6. The medical system of claim 5 wherein the housing is a wearable housing.

7. The medical system of claim 5 wherein the housing is an infusion pump.

8. A medical infusion system comprising:
    a wearable housing;
    at least one non-pressurized at least partially collapsible reservoir for a fluid contained within the housing comprising an integral septum;
    at least one fluid path fluidly connected to the at least one non-pressurized at least partially collapsible reservoir; and
    at least one microneedle fluidly connected to the at least one non-pressurized at least partially collapsible reservoir by the at least one fluid path wherein the at least one fluid path extends through the microneedle, wherein the at least one non-pressurized at least partially collapsible reservoir is fluidly connected to the at least one fluid path by at least one needle penetrating the septum on the at least one non-pressurized at least partially collapsible reservoir, wherein the at least one microneedle having a body portion and at least two appendages, wherein the body portion is made from a first material and the at least two appendages are made from a second material, wherein the second material is different from the first material, wherein the second material is dissolvable, and wherein the at least two appendages provide for microneedle retention.

9. The medical infusion system of claim 8 further comprising at least one microneedle analyte sensor connected to a path, wherein the path is connected to the wearable housing.

10. A medical infusion and sensing system comprising:
a wearable housing;
at least one at least partially collapsible reservoir for a fluid contained within the wearable housing comprising an integral septum;
at least one fluid path fluidly connected to the at least one at least partially collapsible reservoir;
at least one microneedle fluidly connected to the at least one at least partially collapsible reservoir by the fluid path wherein the at least one fluid path extends through the microneedle; and
at least one microneedle analyte sensor attached to a path, the path attached to the housing, wherein the reservoir is fluidly connected to the at least one fluid path by at least one needle penetrating the septum on the reservoir, wherein the at least one microneedle having a body portion and at least two appendages, wherein the body portion is made from a first material and the at least two appendages are made from a second material, wherein the second material is different from the first material, wherein the second material is dissolvable, and wherein the at least two appendages provide for microneedle retention.

11. The medical infusion and sensing system of claim 10 wherein the wearable housing comprising a reusable portion and a disposable portion.

12. The medical infusion and sensing system of claim 10 wherein the at least one at least partially collapsible reservoir comprising at least one flexible portion.

13. The medical infusion and sensing system of claim 10 further comprising a pumping mechanism for pumping fluid from the at least one at least partially collapsible reservoir through the at least one fluid path.

14. The medical infusion and sensing system of claim 13 wherein the pumping mechanism is actuated using at least one shape memory actuator.

\* \* \* \* \*